(12) United States Patent
Boor (10) Patent No.: US 11,135,434 B2
(45) Date of Patent: Oct. 5, 2021

(54) SYSTEMS AND METHODS FOR IMPROVED DAMAGE PROTECTION DURING ELECTROSTATIC DISCHARGE AND CARDIAC DEFIBRILLATION, AND FOR SUBSTANTIALLY IMPROVED STIMULATION INTERFERENCE MITIGATION IN IMPLANTABLE PULSE GENERATORS (71) Applicant: ADVANCED NEUROMODULATION SYSTEMS, INC., Plano, TX (US)

(72) Inventor: Steven Boor, Plano, TX (US)

(73) Assignee: Advanced Neuromodulation Systems, Inc., Plano, TX (US)

(*) Notice: Subject to any disclaimer, the term of this patent is extended or adjusted under 35 U.S.C. 154(b) by 0 days.

(21) Appl. No.: 16/433,975

(22) Filed: Jun. 6, 2019

(65) Prior Publication Data
US 2020/0384274 A1 Dec. 10, 2020

(51) Int. Cl.
*A61N 1/37* (2006.01)
*A61N 1/372* (2006.01)
(Continued)

(52) U.S. Cl.
CPC ........ *A61N 1/3718* (2013.01); *A61N 1/37211* (2013.01); *A61N 1/3931* (2013.01); *A61N 1/025* (2013.01); *A61N 1/3937* (2013.01)

(58) Field of Classification Search
CPC .............. A61N 1/3718; A61N 1/37211; A61N 1/36125; A61N 1/025; A61N 1/3931; A61N 1/3937; A61N 1/08
See application file for complete search history.

(56) References Cited

U.S. PATENT DOCUMENTS 3,968,802 A * 7/1976 Ballis ................. A61N 1/37
607/9
4,320,763 A * 3/1982 Money ................ H02H 9/02
607/9
(Continued)

FOREIGN PATENT DOCUMENTS

WO 2001/093953 A1 12/2001

OTHER PUBLICATIONS

International Search Report and Written Opinion for International Patent Application No. PCT/US2020/031640, dated Aug. 12, 2020, 16 pages.

*Primary Examiner* — Mallika D Fairchild
*Assistant Examiner* — Shreya Anjaria (57) ABSTRACT

The present disclosure provides systems and methods for protection circuitry for an implantable pulse generator (IPG) of a neurostimulation system. The protection circuitry is coupled to an IPG ground, a plurality of electrodes, and an IPG case, and operable to protect IPG stimulation and sensing circuitry from damage during electrostatic discharge and cardiac defibrillation, and to mitigate unintended stimulation during electromagnetic interference. The protection circuitry includes an IPG ground connection, a plurality of protection Zener diodes, wherein one of the protection Zener diodes is electrically coupled between the IPG case and a float Zener diode, and wherein the remaining protection Zener diodes are electrically coupled between the plurality of electrodes and the float Zener diode, and the float Zener diode electrically coupled between the plurality of protection Zener diodes and the IPG ground.

20 Claims, 10 Drawing Sheets

(51) Int. Cl.
*A61N 1/39* (2006.01)
*A61N 1/02* (2006.01)

(56) References Cited

U.S. PATENT DOCUMENTS

| | | | | |
|---|---|---|---|---|
| 4,796,630 | A * | 1/1989 | Regna | A61N 1/37 |
| | | | | 128/908 |
| 5,697,958 | A * | 12/1997 | Paul | A61N 1/37 |
| | | | | 607/31 |
| 5,836,992 | A * | 11/1998 | Thompson | A61N 1/3754 |
| | | | | 607/36 |
| 7,127,294 | B1 * | 10/2006 | Wang | A61N 1/3718 |
| | | | | 607/36 |
| 7,212,110 | B1 | 5/2007 | Martin et al. | |
| 7,228,179 | B2 | 6/2007 | Campen et al. | |
| 7,571,007 | B2 | 8/2009 | Erickson et al. | |
| 7,768,299 | B2 * | 8/2010 | Gupta | H03K 19/00384 |
| | | | | 326/38 |
| 8,498,698 | B2 * | 7/2013 | Donofrio | A61N 1/37 |
| | | | | 607/2 |
| 2006/0170486 | A1 | 8/2006 | Tranchina et al. | |
| 2007/0055308 | A1 * | 3/2007 | Haller | A61N 1/3787 |
| | | | | 607/2 |
| 2012/0194953 | A1 | 8/2012 | Mikolajczak | |
| 2016/0250475 | A1 * | 9/2016 | Marnfeldt | A61N 1/3787 |
| | | | | 607/61 |
| 2017/0113054 | A1 | 4/2017 | Dellamano et al. | |
| 2020/0346005 | A1 | 11/2020 | Boor et al. | |
| 2020/0346014 | A1 | 11/2020 | Boor et al. | |

* cited by examiner

SYSTEMS AND METHODS FOR IMPROVED DAMAGE PROTECTION DURING ELECTROSTATIC DISCHARGE AND CARDIAC DEFIBRILLATION, AND FOR SUBSTANTIALLY IMPROVED STIMULATION INTERFERENCE MITIGATION IN IMPLANTABLE PULSE GENERATORS

A. Field of the Disclosure

The present disclosure relates generally to neurostimulation systems, and more particularly to improved protection of stimulation and sensing circuitry from damage during electrostatic discharge and cardiac defibrillation, and for substantially improved mitigation of stimulation therapy degradation during electromagnetic interference, for implantable pulse generators.

B. Background Art

Neurostimulation is an established neuromodulation therapy for the treatment of movement disorders. For example, neurostimulation has been shown to improve cardinal motor symptoms of Parkinson's Disease (PD), such as bradykinesia, rigidity, and tremors. Types of neurostimulation include deep brain stimulation (DBS) and spinal cord stimulation (SCS).

Neurostimulation systems typically include an implantable pulse generator (IPG). IPGs are generally not immune to interference from magnetic resonance imaging (MRI) systems and other sources of electromagnetic interference (EMI). Accordingly, for at least some known IPGs, neurostimulation therapy is often disabled and the device is placed into an MRI-safe mode of operation while the patient undergoes an MRI scan, or when the patient expects to be subjected to relatively large levels of EMI (e.g., when going through a body scanner and/or metal detector as part of a security screening). For other known IPGs, specialized bipolar stimulation program settings (i.e., those which do not utilize the IPG can/case for stimulation) can be utilized during an MRI scan for maintaining effective and desirable therapy. However, specialized programming places additional burdens on the clinician and/or neurologist in creating such customized stimulation programs and for patient use of them in those interference scenarios.

Accordingly, it would be desirable to provide an IPG that is capable of maintaining effective and desirable neurostimulation therapy even while experiencing interference from MRI systems and/or other sources of EMI, without requiring the use of specialized stimulation programs or settings.

BRIEF SUMMARY OF THE DISCLOSURE

In one embodiment, the present disclosure is directed to protection circuitry for an implantable pulse generator (IPG) of a neurostimulation system. The protection circuitry is coupled to an IPG ground, a plurality of electrodes, and an IPG case, and operable to protect IPG stimulation and sensing circuitry from damage during electrostatic discharge and cardiac defibrillation, and to mitigate unintended stimulation during electromagnetic interference. The protection circuitry includes an IPG ground connection, a plurality of protection Zener diodes, wherein one of the protection Zener diodes is electrically coupled between the IPG case and a float Zener diode, and wherein the remaining protection Zener diodes are electrically coupled between the plurality of electrodes and the float Zener diode, and the float Zener diode electrically coupled between the plurality of protection Zener diodes and the IPG ground.

In another embodiment, the present disclosure is directed to a neurostimulation system. The neurostimulation system includes an implantable pulse generator (IPG) ground, an IPG case, a stimulation lead comprising a plurality of electrodes, and an IPG coupled to the IPG ground, the IPG case, and the stimulation lead, the IPG including protection circuitry operable to protect IPG stimulation and sensing circuitry from damage due to electrostatic discharge and cardiac defibrillation, and to mitigate unintended stimulation during electromagnetic interference. The protection circuitry includes an IPG ground connection, a plurality of protection Zener diodes, wherein one of the protection Zener diodes is electrically coupled between the IPG case and a float Zener diode, and wherein the remaining protection Zener diodes are electrically coupled between the plurality of electrodes and the float Zener diode, and the float Zener diode electrically coupled between the plurality of protection Zener diodes and the IPG ground.

In another embodiment, the present disclosure is directed to a method of assembling protection circuitry for an implantable pulse generator (IPG) of a neurostimulation system including an IPG ground, a plurality of electrodes, and an IPG case. The method includes providing an IPG ground connection, electrically coupling one of a plurality of protection Zener diodes between the IPG case and a float Zener diode, electrically coupling the remaining protection Zener diodes between the plurality of electrodes and the float Zener diode, and electrically coupling the float Zener diode between the plurality of protection Zener diodes and the IPG ground.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The present disclosure provides systems and methods for improved protection circuitry for an implantable pulse generator (IPG) of a neurostimulation system. The improved protection circuitry is coupled to an IPG ground, a plurality of electrodes, and an IPG case, and operable to protect IPG stimulation and sensing circuitry from damage during electrostatic discharge and cardiac defibrillation, and to mitigate unintended stimulation during electromagnetic interference. The improved protection circuitry includes an IPG ground connection and a plurality of protection Zener diodes. One of the protection Zener diodes is electrically coupled between the IPG case and a float Zener diode, and the remaining protection Zener diodes are electrically coupled between the plurality of electrodes and the float Zener diode. The float Zener diode is electrically coupled between the plurality of protection Zener diodes and the IPG ground.

The improved protection circuitry described herein also exhibits a substantial advantage in imposing a minimal increase in IPG manufacturing costs and assembly complexity, because only a single additional component (i.e., the float Zener diode) is required in the bill of material (BOM) for the construction of the IPG. Accordingly, the improved protection circuitry provides a simple and cost-effective solution to a relatively complex and difficult MRI/EMI problem.

Neurostimulation systems are devices that generate electrical pulses and deliver the pulses to nervous tissue of a patient to treat a variety of disorders. One category of neurostimulation systems is deep brain stimulation (DBS). In DBS, pulses of electrical current are delivered to target regions of a subject's brain, for example, for the treatment of movement and effective disorders such as PD and essential tremor. Another category of neurostimulation systems is spinal cord stimulation (SCS).

Neurostimulation systems generally include a pulse generator and one or more leads. A stimulation lead includes a lead body of insulative material that encloses wire conductors. The distal end of the stimulation lead includes multiple electrodes, or contacts, that intimately impinge upon patient tissue and are electrically coupled to the wire conductors. The proximal end of the lead body includes multiple terminals (also electrically coupled to the wire conductors) that are adapted to receive electrical pulses. In DBS systems, the distal end of the stimulation lead is implanted within the brain tissue to deliver the electrical pulses. The stimulation leads are then tunneled to another location within the patient's body to be electrically connected with a pulse generator or, alternatively, to an "extension." The pulse generator is typically implanted in the patient within a subcutaneous pocket created during the implantation procedure.

The pulse generator is typically implemented using a metallic housing (or can) that encloses circuitry for generating the electrical stimulation pulses, control circuitry, communication circuitry, a rechargeable battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on the proximal end of a stimulation lead.

Figure 1:
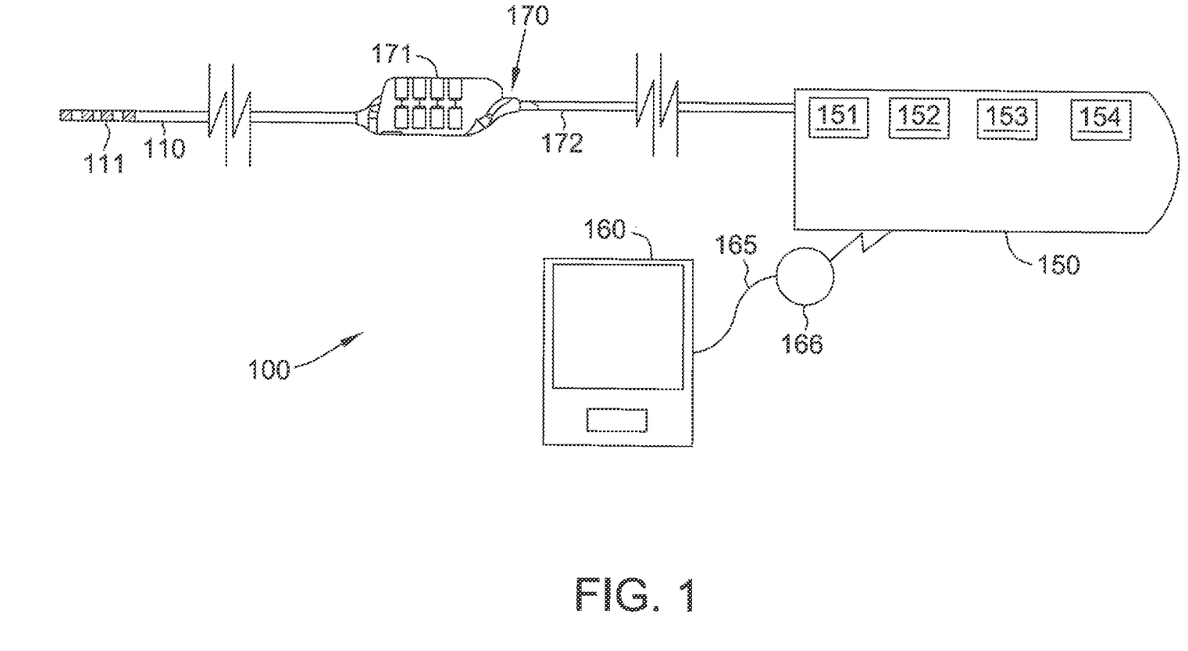
FIG. 1 is a schematic view of one embodiment of a stimulation system.

Referring now to the drawings, and in particular to FIG. 1, a stimulation system is indicated generally at 100. Stimulation system 100 generates electrical pulses for application to tissue of a patient, or subject, according to one embodiment. System 100 includes an implantable pulse generator (IPG) 150 that is adapted to generate electrical pulses for application to tissue of a patient. Alternatively, system 100 may include an external pulse generator (EPG) positioned outside the patient's body. IPG 150 typically includes a metallic housing (or can) that encloses a controller 151, pulse generating circuitry 152, a battery 153, far-field and/or near field communication circuitry 154, and other appropriate circuitry and components of the device. Controller 151 typically includes a microcontroller or other suitable processor for controlling the various other components of the device. Software code is typically stored in memory of IPG 150 for execution by the microcontroller or processor to control the various components of the device.

IPG 150 may comprise one or more attached extension components 170 or be connected to one or more separate extension components 170. Alternatively, one or more stimulation leads 110 may be connected directly to IPG 150. Within IPG 150, electrical pulses are generated by pulse generating circuitry 152 and are provided to switching circuitry. The switching circuit connects to output wires, traces, lines, or the like (not shown) which are, in turn, electrically coupled to internal conductive wires (not shown) of a lead body 172 of extension component 170. The conductive wires, in turn, are electrically coupled to electrical connectors (e.g., "Bal-Seal" connectors) within connector portion 171 of extension component 170. The terminals of one or more stimulation leads 110 are inserted within connector portion 171 for electrical connection with respective connectors. Thereby, the pulses originating from IPG 150 and conducted through the conductors of lead body 172 are provided to stimulation lead 110. The pulses are then conducted through the conductors of lead 110 and applied to tissue of a patient via electrodes 111. Any suitable known or later developed design may be employed for connector portion 171.

For implementation of the components within IPG 150, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 2006/0170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within IPG 150. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed, such as constant voltage pulse generating circuitry.

Stimulation lead(s) 110 may include a lead body of insulative material about a plurality of conductors within the material that extend from a proximal end of lead 110 to its distal end. The conductors electrically couple a plurality of electrodes 111 to a plurality of terminals (not shown) of lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally or alternatively, various sensors (not shown) may be located near the distal end of stimulation lead 110 and electrically coupled to terminals through conductors within the lead body 172. Stimulation lead 110 may include any suitable number and type of electrodes 111, terminals, and internal conductors.

Controller device 160 may be implemented to recharge battery 153 of IPG 150 (although a separate recharging device could alternatively be employed). A "wand" 165 may be electrically connected to controller device 160 through suitable electrical connectors (not shown). The electrical connectors are electrically connected to coil 166 (the "primary" coil) at the distal end of wand 165 through respective wires (not shown). Typically, coil 166 is connected to the wires through capacitors (not shown). Also, in some embodiments, wand 165 may comprise one or more temperature sensors for use during charging operations.

The patient then places the primary coil 166 against the patient's body immediately above the secondary coil (not shown), i.e., the coil of the implantable medical device. Preferably, the primary coil 166 and the secondary coil are aligned in a coaxial manner by the patient for efficiency of the coupling between the primary and secondary coils. Controller device 160 generates an AC-signal to drive current through coil 166 of wand 165. Assuming that primary coil 166 and secondary coil are suitably positioned relative to each other, the secondary coil is disposed within the magnetic field generated by the current driven through primary coil 166. Current is then induced by a magnetic field in the secondary coil. The current induced in the coil of the implantable pulse generator is rectified and regulated to recharge the battery of IPG 150. The charging circuitry may also communicate status messages to controller device 160 during charging operations using pulse-loading or any other suitable technique. For example, controller device 160 may communicate the coupling status, charging status, charge completion status, etc.

External controller device 160 is also a device that permits the operations of IPG 150 to be controlled by a user after IPG 150 is implanted within a patient, although in alternative embodiments separate devices are employed for charging and programming. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with IPG 150.

Controller device 160 preferably provides one or more user interfaces to allow the user to operate IPG 150 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. In the methods and systems described herein, stimulation parameters may include, for example, a number of pulses in a burst (e.g., 3, 4, or 5 pulses per burst), an intra-burst frequency (e.g., 500 Hz), an inter-burst frequency (e.g., 40 Hz), and a delay between the pulses in a burst (e.g., less than 1 millisecond (ms)).

IPG 150 modifies its internal parameters in response to the control signals from controller device 160 to vary the stimulation characteristics of stimulation pulses transmitted through stimulation lead 110 to the tissue of the patient. Neurostimulation systems, stimsets, and multi-stimset programs are discussed in PCT Publication No. WO 2001/093953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference. Example commercially available neurostimulation systems include the EON MINI™ pulse generator and RAPID PROGRAMMER™ device from Abbott Laboratories.

The systems and methods described herein provide protection circuitry that provides improved protection for stimulation and sensing circuitry during heart defibrillation and/or electrostatic discharge transients. Further, the improved IPG protection circuitry described herein enhances the IPG's capability of maintaining safe and effective neurostimulation therapy for patients during an MRI scan and other EMI events. The systems and methods described herein are particularly useful in SCS systems, but may also be used in other neurostimulation systems (e.g., DBS systems). Specifically, the improved IPG protection circuitry described herein overcomes therapy degradation concerns and other concerns related to relatively large interference voltages being generated on IPG leads from MRI and/or other EMI, providing substantial benefits for clinicians, neurologists, and patients. The systems and methods described herein also enable using a stimulation current regulator powered by a floating power supply. This enables maintaining effective and safe stimulation therapy during MRI and/or other EMI for patients who use relatively strong stimulation settings (described in detail herein). An example and discussion of "floating power supply" powered current regulator circuitry is provided in U.S. patent application Ser. No. 16/401,971, which is incorporated herein by reference in its entirety.

During MRI or other EMI, to avoid degradation of stimulation therapy, to avoid unintended stimulation, and to avoid other IPG performance concerns, a high-impedance electrical loop must be maintained between a case or can of IPG 150 and all of the electrodes in the stimulation lead. For example, during an MRI scan, induced interference voltages on the electrodes may reach levels as high as +/−10.8 Volts in implantable SCS devices. At least some known systems handle this interference by forcing patients to disable stimulation therapy during the exposure to interference, or to utilize a customized bipolar stimulation program for maintaining effective and desired therapy under interference conditions.

In contrast, the systems and methods described herein allow stimulation and sensing circuitry in IPG 150 to be voltage level shifted above or below the IPG ground as interference is detected. This allows for automatic compensation of induced interference voltages, and it allows stimulation therapy to be maintained during exposure to interference without the need for additional stimulation programs customized exclusively for use during MRI/EMI exposure.

Figure 2:
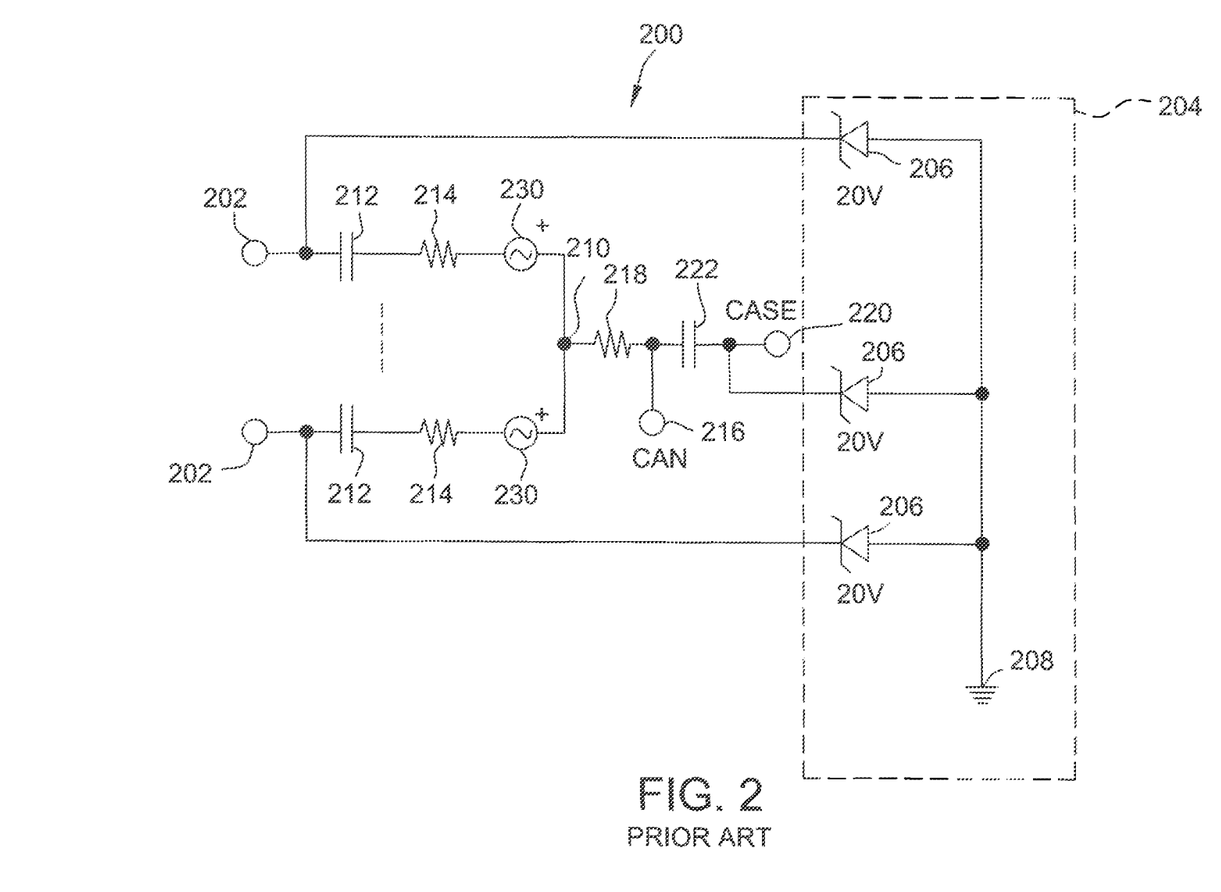
FIG. 2 is a circuit diagram of prior art implantable pulse generator (IPG) circuitry using known protection circuitry, and an electrical model for the electrode/tissue load network.

FIG. 2 is a circuit diagram of IPG circuitry 200 using known protection circuitry 204. IPG circuitry 200 includes an IPG case 220, a plurality of electrodes 202, and known protection circuitry 204. Known protection circuitry 204 includes a plurality of protection Zener diodes 206 directly electrically coupled to an IPG ground 208 (e.g., a negative battery terminal). Each electrode 202 and IPG case 220 is electrically coupled to IPG ground 208 through an associated protection Zener diode 206. Protection Zener diodes 206 typically have a reverse breakdown voltage of 20 Volts.

As shown in circuit schematic of FIG. 2, each electrode 202 is electrically coupled to a common node 210 through a respective first capacitor 212 and respective first resistor 214. Further, common node 210 is electrically coupled to a can electrode 216 through a second resistor 218, and can electrode 216 is electrically coupled to IPG case 220 through a second capacitor 222. IPG case 220 is electrically coupled to IPG ground 208 through a protection Zener diode 206. Interference voltage 230 (e.g., resulting from MRI or other EMI) is also represented in the schematic diagram of IPG circuitry 200.

Notably, known protection circuitry 204 in FIG. 2 does not allow for the compensation of large interference voltages while delivering stimulation therapy, especially at relatively strong stimulation settings. Relatively strong stimulation settings, as used herein, may include, for example, large amplitude stimulation. For example strong stimulation settings may include applying stimulation currents in a range from 10-20 milliamperes (mA) (which may result in voltages in a range from 10-15 Volts across tissue, electrodes, etc.), whereas more typical stimulation settings may include applying stimulation currents in a range from 2-5 mA.

Figure 3:
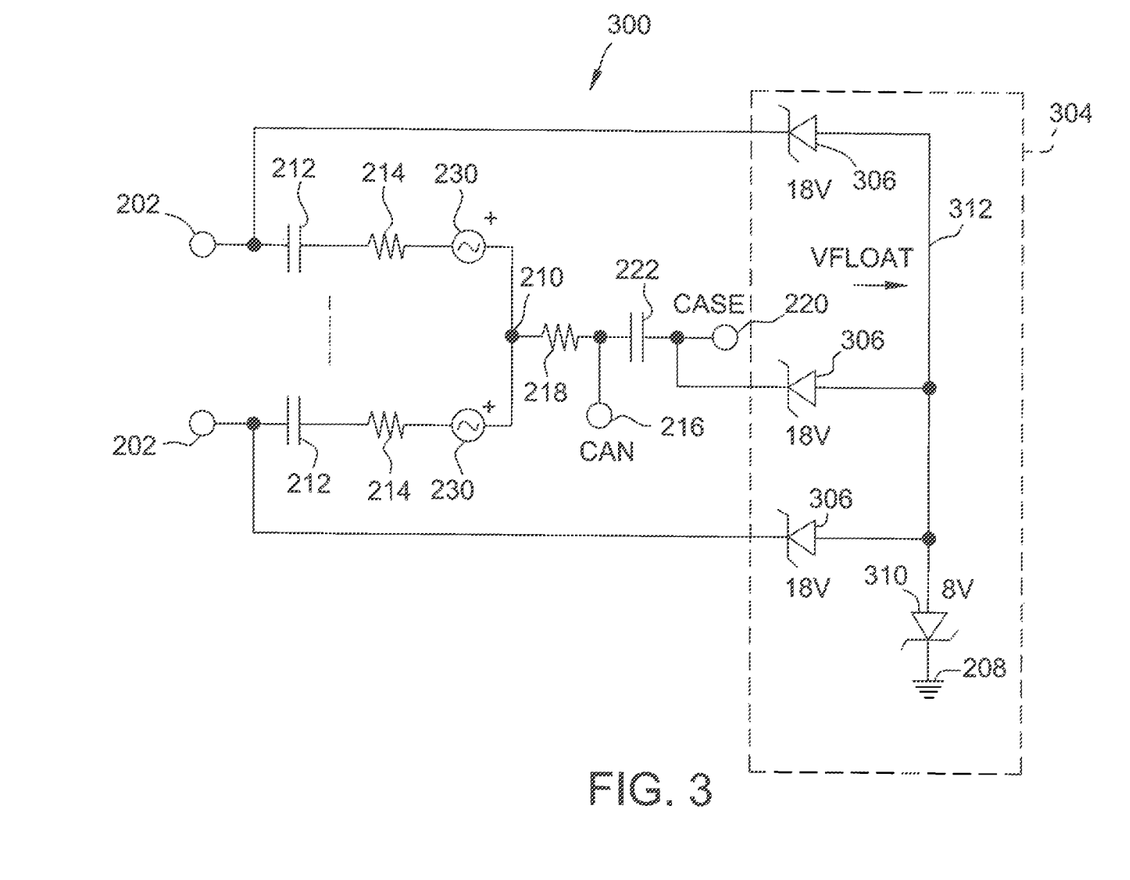
FIG. 3 is a circuit diagram of one embodiment of IPG circuitry using improved protection circuitry that may be used with the stimulation system shown in FIG. 1, and an electrical model for the electrode tissue/load network.

FIG. 3 is a circuit diagram of one embodiment of IPG circuitry 300 using improved protection circuitry 304 in accordance with the systems and methods described herein. IPG circuitry 300 may be implemented within, for example, IPG 150 (shown in FIG. 1). IPG circuitry 300 provides substantial performance improvements over IPG circuitry 200, as described in detail herein. For IPG circuitry 200 and IPG circuitry 300, like components are labeled with like reference numerals.

IPG circuitry 300 includes improved protection circuitry 304 including a plurality of protection Zener diodes 306. However, in contrast to protection Zener diodes 206 (shown in FIG. 2), in this embodiment, protection Zener diodes 306 have a reverse breakdown voltage of 18 Volts (instead of 20 Volts). The lower reverse breakdown voltage for protection Zener diodes 306 results in improved device protection and reliability for IPG 150. Specifically, the lower reverse breakdown voltage results in improved IPG reliability via reduced heating of protection Zener diodes 306 during cardiac defibrillation or electrostatic discharge events, which may induce relatively high currents through protection Zener diodes 306.

As shown in FIG. 3, improved protection circuitry 304 also includes a float Zener diode 310 electrically coupled between IPG case 220, protection Zener diodes 306, and IPG ground 208. Float Zener diode 310 is coupled in a reverse orientation relative to protection Zener diodes 306 (i.e., the anode of float Zener diode 310 is directly coupled to the commonly-connected anode terminals of protection Zener diodes 306). In this embodiment, float Zener diode 310 has a reverse breakdown voltage of 8 Volts. Alternatively, float Zener diode 310 may have any suitable reverse breakdown voltage. Notably, during cardiac defibrillation or electrostatic discharge events, relatively little current flows through float Zener diode 310 because IPG ground 208 is substantially unaffected by those events.

The inclusion of float Zener diode 310 in improved protection circuitry 304 results in a floating node 312 (VFLOAT) at the connection between float Zener diode 310 and protection Zener diodes 306. Floating node 312 floats up and down based on the magnitude of interference 230 (and allows protection Zener diodes 306 to float up and down with respect to IPG ground 208). This substantially mitigates reverse breakdown current conduction of protection Zener diodes 306, which alleviates unintended stimulation currents from flowing through IPG 150 and patient tissue. Further, if one of electrodes 202 experiences significant electromagnetic interference, floating node 312 helps to protect the IPG stimulation and sensing circuitry connected to electrodes 202 from being damaged. Floating node 312 also helps to protect the IPG stimulation and sensing circuitry connected to electrodes 202 in the event of electrostatic discharge and cardiac defibrillation between electrodes 202 and/or can electrode 216.

Further, floating node 312 enables a floating power supply (e.g., for powering a stimulation current regulator in IPG 150) to be biased by a common-mode voltage source above or below IPG ground 208. That common-mode voltage source may be used to automatically compensate for large induced voltages from interference 230 caused by MRI or other EMI, all while consuming relatively little additional battery current. For example, the determination of when and how much to compensate for the induced interference voltages can be performed using one or more low-power voltage comparator circuits (not shown) that receive inputs from an EMI antenna or from a Kelvin-connect electrode that is not used for stimulation therapy and from an IPG case connection (e.g., IPG case 220). An example and discussion of the use of an EMI antenna or a "Kelvin-connect electrode" for monitoring interference from MRI/EMI is provided in U.S. patent application Ser. No. 16/401,943, which is incorporated herein by reference in its entirety.

Figure 4:
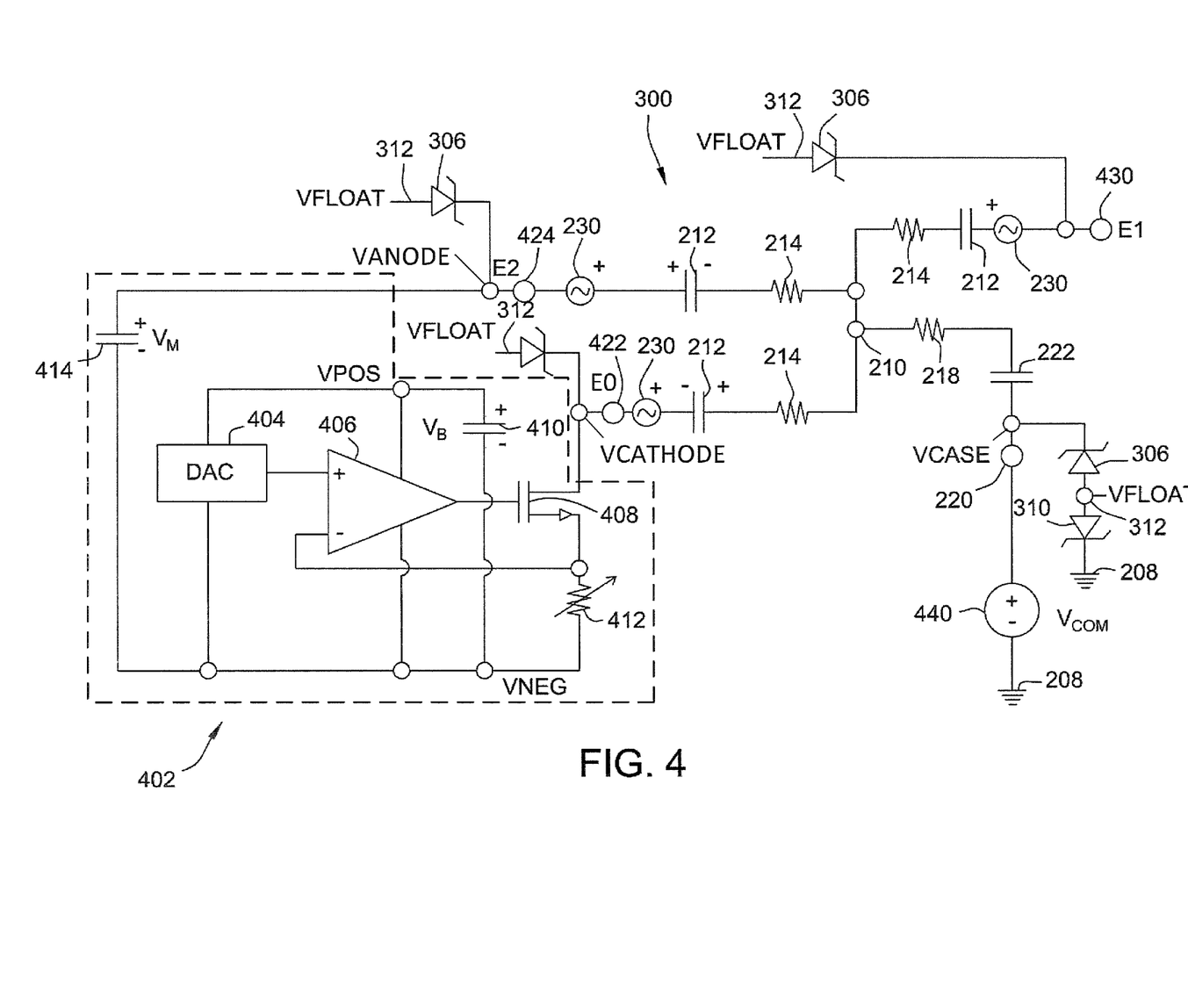
FIG. 4 is a circuit diagram of the IPG circuitry using the improved protection circuitry shown in FIG. 3 in combination with a stimulation current regulator, and an electrical model for the electrode/tissue load network during stimulation.

FIG. 4 is a circuit diagram of IPG circuitry 300 configured to operate in a mode for delivering stimulation therapy in combination with a stimulation current regulator 402. IPG circuitry 300 and stimulation current regulator 402 may be implemented, for example, in an IPG of a bipolar SCS system that includes a single anode (at $V_{ANODE}$) and a single cathode (at $V_{CATHODE}$). Stimulation current regulator 402 includes a digital to analog converter (DAC) 404, an error amplifier 406, a high-impedance stimulation current conducting device 408 (e.g., a MOSFET), a floating power supply ($V_B$) 410, a variable resistor 412, and a voltage multiplier 414 ($V_M$). DAC 404, error amplifier 406 and floating power supply 410 may be operative based on voltages provided as VPOS and VNEG as shown in FIG. 4. A common-mode voltage source 440 (VCOM) may be used to bias stimulation current regulator 402 above or below IPG ground 208 during interference from MRI/EMI.

In this embodiment, in addition to a first stimulation electrode 422 (E0) and a second stimulation electrode 424 (E2), IPG circuitry 300 further includes a non-active electrode 430 (E1) (i.e., an electrode that is not used for stimulation). Non-active electrode 430 may be a Kelvin-connect electrode that is used to monitor electromagnetic interference in IPG circuitry 300, as noted above. Alternatively, an EMI antenna may be used to monitor electromagnetic interference, as noted above. In embodiments where an EMI antenna is utilized to monitor electromagnetic interference, the neurostimulation circuitry electrically connected to the EMI antenna should also be protected from static damage and cardiac defibrillation. This can be readily achieved via an electrical connection to the cathode terminal of a Zener protection diode, in the very same manner described above which is used for the protection of the neurostimulator system connections to the electrodes in a stimulation lead.

Further, common-mode voltage source 440 (VCOM) is shown connected between IPG case 220 and IPG ground 208. A case voltage (VCASE) and a common voltage (at common node 210) may be adjusted over time based on how much interference is detected using an EMI antenna or non-active electrode 430 and IPG case 220. As shown in FIG. 4, an anode of each protection Zener diode 306 is connected to floating node 312 (VFLOAT). For mitigation of undesirable stimulation interference caused by MRI/EMI events, this embodiment may operate in tandem with methods and system for operating stimulation current regulator 402 from a floating power supply, as described in U.S. patent application Ser. No. 16/401,971.

Figure 5A:
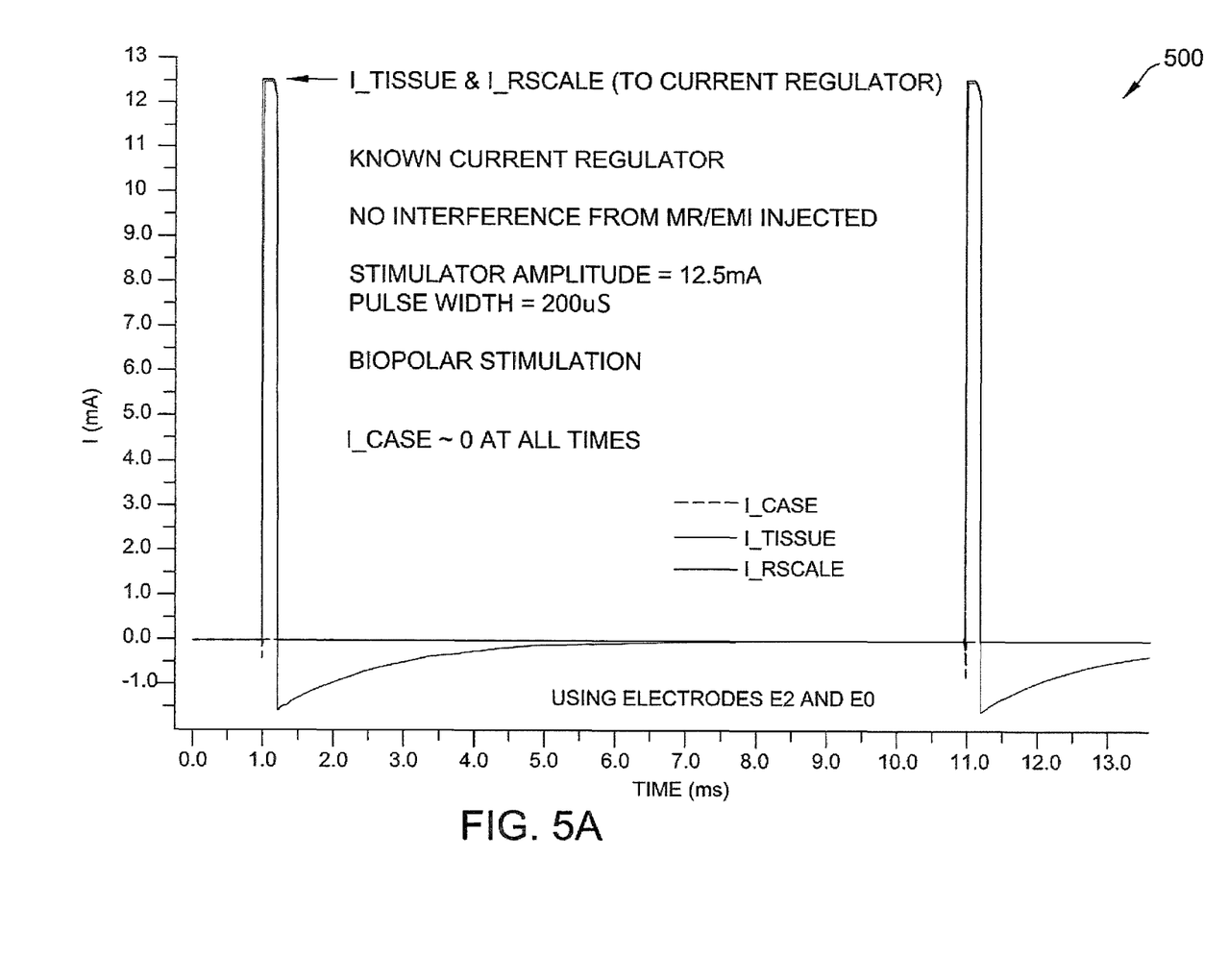
FIGS. 5A and 5B are graphs showing experimental values for currents and voltages of the IPG circuitry and patient tissue using the known protection circuitry shown in FIG. 2 while applying SCS therapy in the absence of electromagnetic interference.
Figure 5B:
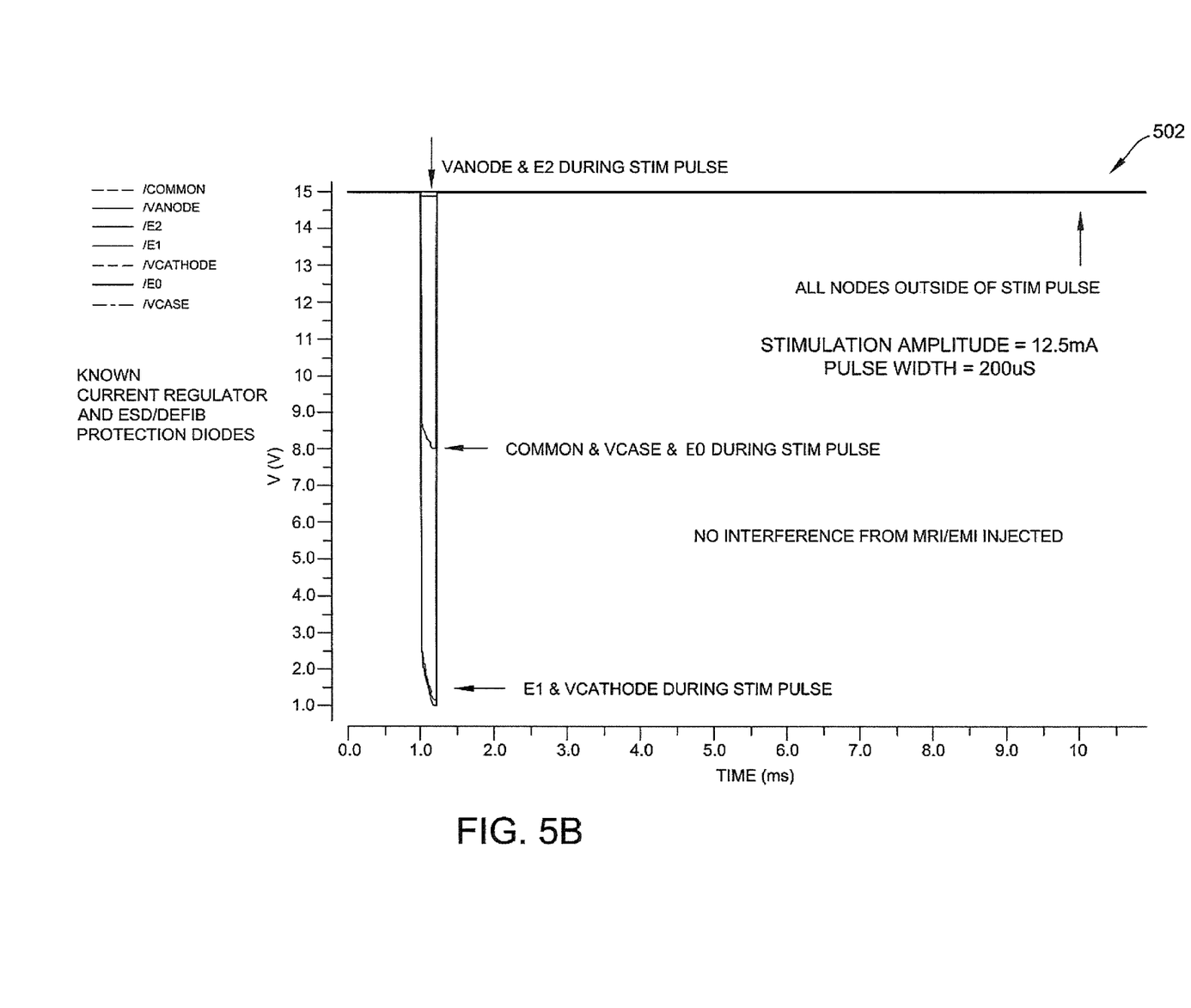
Figure 6A:
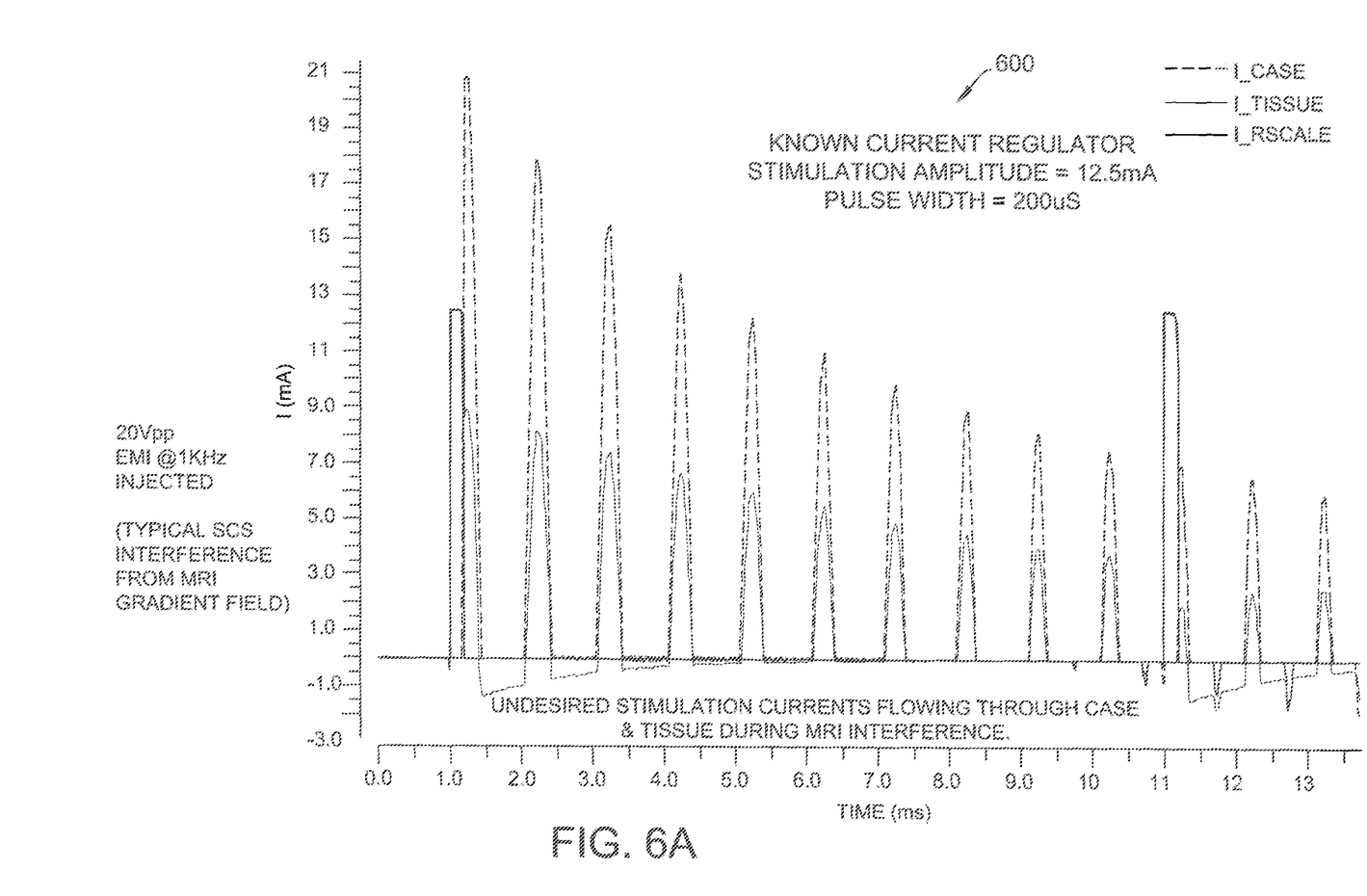
FIGS. 6A and 6B are graphs showing experimental values for currents and voltages of the IPG circuitry and patient tissue using the known protection circuitry shown in FIG. 2 while simultaneously applying SCS therapy and experiencing electromagnetic interference.
Figure 6B:
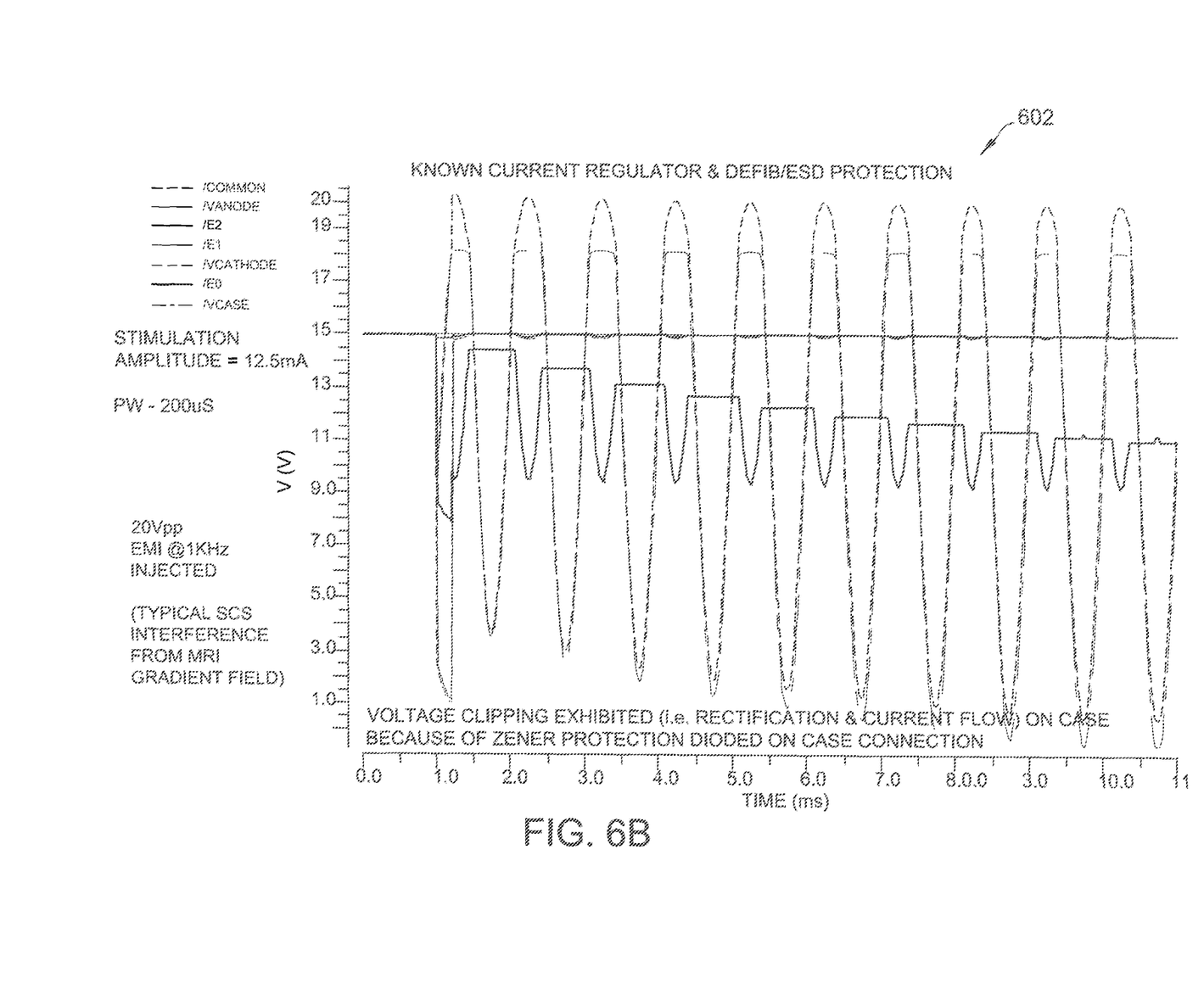
Figure 7A:
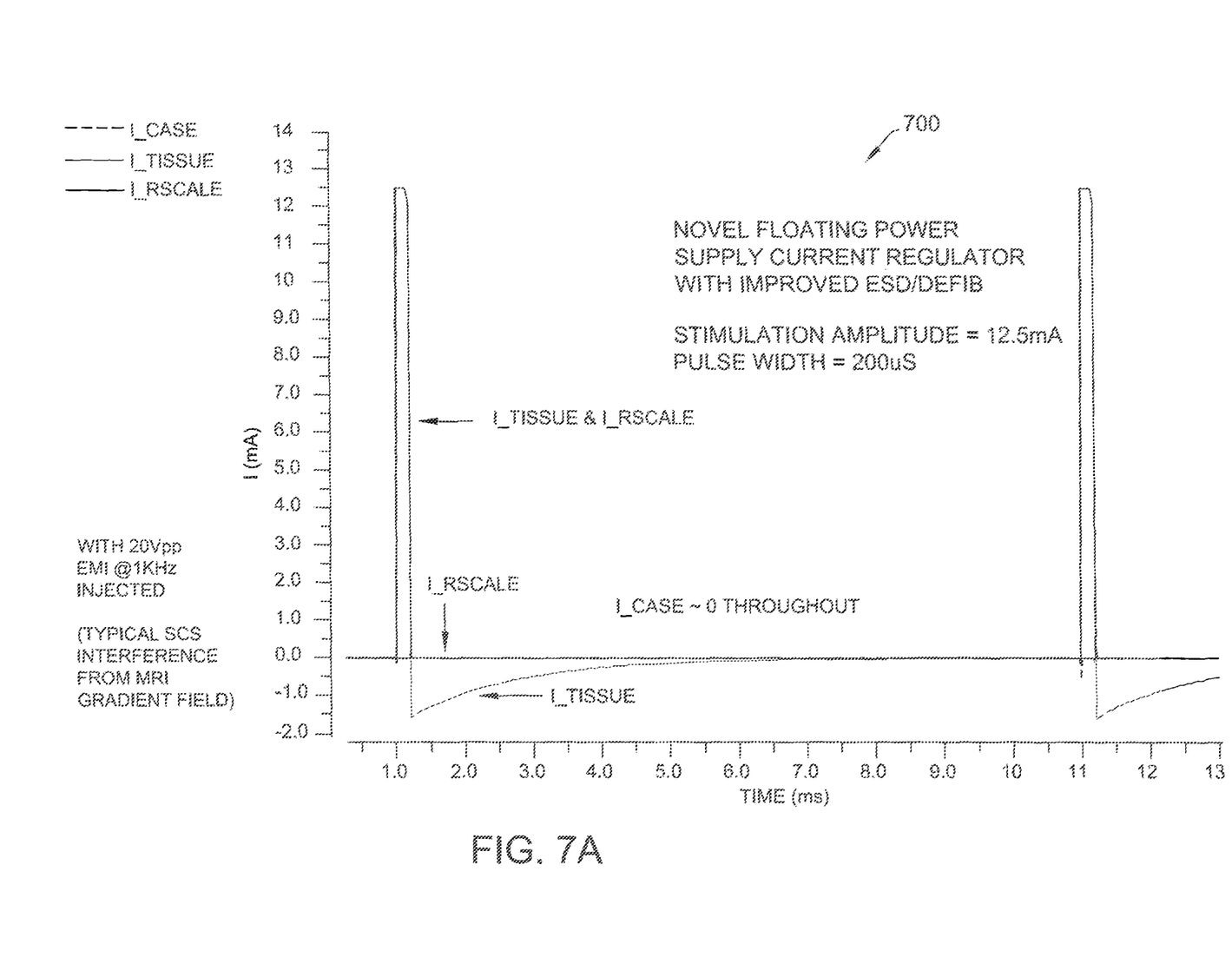
FIGS. 7A and 7B are graphs showing experimental values for currents and voltages of the IPG circuitry and patient tissue using the improved protection circuitry shown in FIG. 3 while simultaneously applying SCS therapy and experiencing electromagnetic interference under the same experimental conditions used to generate FIGS. 6A and 6B.
Figure 7B:
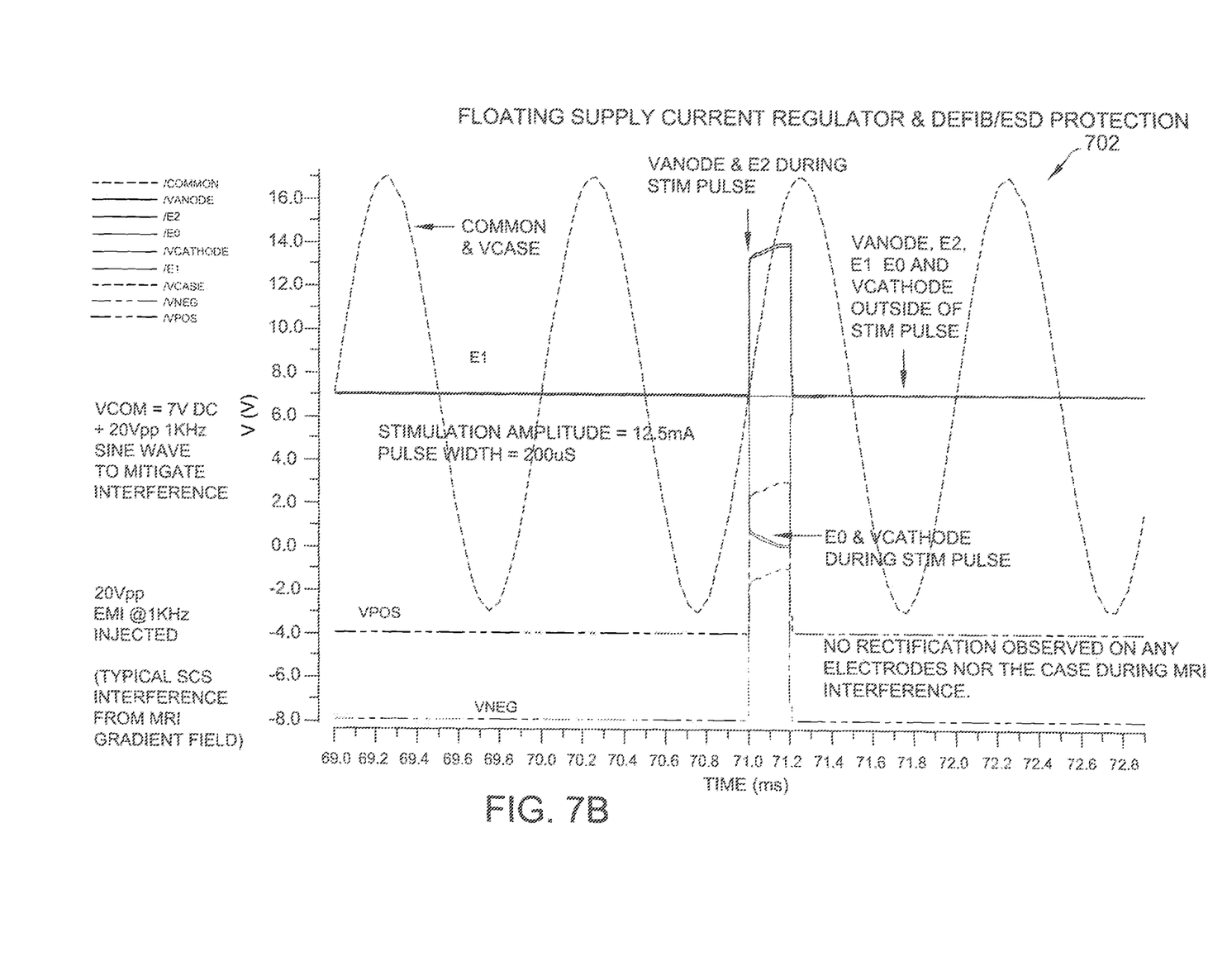

FIGS. 5A and 5B are graphs 500 and 502 showing experimental values for currents and voltages, respectively, using known IPG protection circuitry (i.e., as shown in FIG. 2) while applying stimulation therapy in the absence of interference. FIGS. 6A and 6B are graphs 600 and 602 showing experimental values for undesirable currents and voltages, respectively, using known IPG protection circuitry while simultaneously applying SCS therapy and experiencing interference typically induced during an MRI scan. Further, FIGS. 7A and 7B are graphs 700 and 702 showing experimental values for currents and voltages, respectively, using the improved IPG protection circuitry described herein (i.e., as shown in FIG. 3) while simultaneously applying the same SCS therapy and experiencing the same level of interference. In these examples, the SCS therapy is applied using relatively strong stimulation settings (e.g., with a stimulation amplitude of 12.5 mA and a pulse width of 200 microseconds (µs)).

As shown in graphs 500 and 502, the stimulation currents and voltages are well-controlled using known IPG protection circuitry (i.e., as shown in FIG. 2) when no interference is present. However, as shown in graphs 600 and 602, undesirable currents and voltages are generated in known IPG circuitry and patient tissue when stimulation is applied and interference is present.

Notably, as shown in graphs 700 and 702, even when interference is present, stimulation currents and voltages are well-controlled in the IPG circuitry and patient tissue using the improved IPG protection circuitry described herein (i.e., as shown in FIG. 3). Specifically, the stimulation currents in graph 700 (where interference is present) are similar to the currents in graph 500 (where no interference is present), which confirms substantially increased immunity to interference from MRI/EMI for the improved protection circuitry.

Further, the voltages shown in graph 702 are indicative that the protection Zener diodes and/or the floating Zener diode in the improved IPG protection circuitry have enough "operating headroom" for remaining in a reverse-biased state throughout the duration of many MRI/EMI events (i.e., they do not exhibit reverse breakdown current conduction). This improved electrical behavior of the Zener diodes is important for mitigating undesirable stimulation currents which would otherwise degrade the effectiveness and/or comfort of neurostimulation therapy for patients during MRI/EMI.

Accordingly, the improved protection provided by IPG circuitry 300 (and, in particular, improved protection circuitry 304) allows IPG 150 to maintain effective and safe stimulation therapy, even during exposure to electromagnetic interference. This substantially improved functionality enhances the robustness, comfort, and satisfaction of stimulation therapy for patients, as well as overall IPG device performance and reliability. In addition, improved protection circuitry 300 helps to reduce the programming burdens of clinicians and neurologists, and simplifies stimulation therapy program usage for patients.

The embodiments described herein provide systems and methods for improved protection circuitry in an implantable pulse generator (IPG) of a neurostimulation system. The improved protection circuitry is coupled to an IPG ground, a plurality of electrodes, and an IPG case, and operable to protect IPG stimulation and sensing circuitry from damage during electrostatic discharge and cardiac defibrillation, and to mitigate unintended stimulation during electromagnetic interference. The improved protection circuitry includes an IPG ground connection and a plurality of protection Zener diodes. One of the protection Zener diodes is electrically coupled between the IPG case and a float Zener diode, and the remaining protection Zener diodes are electrically coupled between the plurality of electrodes and the float Zener diode. The float Zener diode is electrically coupled between the plurality of protection Zener diodes and the IPG ground.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. Protection circuitry for an implantable pulse generator (IPG) of a neurostimulation system, the protection circuitry coupled to an IPG ground, a plurality of electrodes, and an IPG case, and operable to protect IPG stimulation and sensing circuitry from damage during electrostatic discharge and cardiac defibrillation, and to mitigate unintended stimulation during electromagnetic interference, the protection circuitry comprising:
a float Zener diode electrically coupled to the IPG ground;
a plurality of protection Zener diodes, wherein one of the protection Zener diodes is electrically coupled between the IPG case and the float Zener diode disposed in an IPG ground connection, and wherein remaining protection Zener diodes are electrically coupled between the plurality of electrodes and the float Zener diode, respectively; and
a common-mode voltage source electrically coupled between the IPG case and the IPG ground, the common-mode voltage source disposed in parallel relative to the IPG ground connection of the float Zener diode and the protection Zener diode electrically coupled to the IPG case.

2. The protection circuitry of claim 1, wherein the plurality of protection Zener diodes each have a reverse breakdown voltage of 18 Volts.

3. The protection circuitry of claim 1, wherein the float Zener diode has a reverse breakdown voltage of 8 Volts.

4. The protection circuitry of claim 1, wherein an anode of the float Zener diode is connected to anodes of each of the plurality of protection Zener diodes.

5. The protection circuitry of claim 1, wherein the IPG is coupled to a stimulation lead having the plurality of electrodes, the stimulation lead operative with the stimulation and sensing circuitry provided as part of the implantable pulse generator of at least one of a spinal cord stimulation (SCS) system and a deep brain stimulation (DBS) system.

6. The protection circuitry of claim 1, wherein the protection circuitry is electrically connected to the IPG case and an EMI antenna or at least one non-active electrode configured to monitor electromagnetic interference.

7. The protection circuitry of claim 1, wherein the protection circuitry is configured to be electrically coupled to a stimulation current regulator.

8. A neurostimulation system comprising:
an implantable pulse generator (IPG) ground;
an IPG case;
a stimulation lead comprising a plurality of electrodes; and
an IPG coupled to the IPG ground, the IPG case, and the stimulation lead, the IPG comprising protection circuitry operable to protect IPG stimulation and sensing circuitry from damage due to electrostatic discharge and cardiac defibrillation, and to mitigate unintended stimulation during electromagnetic interference, the protection circuitry comprising:
a float Zener node electrically coupled to the IPG ground;
a plurality of protection Zener diodes, wherein one of the protection Zener diodes is electrically coupled between the IPG case and the float Zener diode disposed in an IPG ground connection, and wherein remaining protection Zener diodes are electrically coupled between the plurality of electrodes and the float Zener diode, respectively; and
a common-mode voltage source electrically coupled between the IPG case and the IPG ground, the common-mode voltage source disposed in parallel relative to the IPG ground connection of the float Zener diode and the protection Zener diode electrically coupled to the IPG case.

9. The neurostimulation system of claim 8, wherein the plurality of protection Zener diodes each have a reverse breakdown voltage of 18 Volts.

10. The neurostimulation system of claim 8, wherein the float Zener diode has a reverse breakdown voltage of 8 Volts.

11. The neurostimulation system of claim 8, wherein an anode of the float Zener diode is connected to anodes of each of the plurality of protection Zener diodes.

12. The neurostimulation system of claim 8, wherein the IPG is operative with at least one of a spinal cord stimulation (SCS) system and a deep brain stimulation (DBS) system.

13. The neurostimulation system of claim 8, wherein the IPG case and an EMI antenna or at least one non-active electrode are electrically connected to the protection circuitry and are configured to monitor electromagnetic interference.

14. The neurostimulation system of claim 8, wherein the IPG further comprises a stimulation current regulator electrically coupled to the protection circuitry.

15. A method of assembling protection circuitry for an implantable pulse generator (IPG) of a neurostimulation system including an IPG ground, a plurality of electrodes, and an IPG case, the method comprising:
electrically coupling a float Zener node to the IPG ground;
providing an IPG ground connection;
electrically coupling one of a plurality of protection Zener diodes between the IPG case and the float Zener diode disposed in the IPG ground connection;
electrically coupling remaining protection Zener diodes between the plurality of electrodes and the float Zener diode, respectively; and
electrically coupling a common-mode voltage source between the IPG case and the IPG ground, the common-mode voltage source disposed in parallel relative to the IPG ground connection of the float Zener diode and the protection Zener diode electrically coupled to the IPG case.

16. The method of claim 15, wherein the plurality of protection Zener diodes each have a reverse breakdown voltage of 18 Volts.

17. The method of claim 15, wherein the float Zener diode has a reverse breakdown voltage of 8 Volts.

18. The method of claim 15, wherein electrically coupling a float Zener diode comprises electrically coupling an anode of the float Zener diode to anodes of each of the plurality of protection Zener diodes.

19. The method of claim 15, wherein the IPG case and an EMI antenna or at least one non-active electrode are electrically connected to the protection circuitry and are configured to monitor electromagnetic interference.

20. The method of claim 15, further comprising electrically coupling the protection circuitry to a stimulation current regulator.

* * * * *